United States Patent [19]

Fujioka et al.

[11] Patent Number: 4,751,933
[45] Date of Patent: Jun. 21, 1988

[54] USE OF HYDROXYBORNYLOXYBUTANES IN AUGMENTING OR ENHANCING THE AROMA OR TASTE OF SMOKING TOBACCO ARTICLES AND SMOKING TOBACCO COMPOSITIONS

[75] Inventors: Futoshi Fujioka, Wanamassa; Richard M. Boden, Ocean; William L. Schreiber, Jackson, all of N.J.

[73] Assignee: International Flavors & Fragrances Inc., New York, N.Y.

[21] Appl. No.: 2,022

[22] Filed: Jan. 9, 1987

Related U.S. Application Data

[60] Division of Ser. No. 837,348, Mar. 7, 1986, Pat. No. 4,668,431, which is a continuation-in-part of Ser. No. 784,618, Oct. 4, 1985, Pat. No. 4,620,041, which is a division of Ser. No. 644,054, Aug. 24, 1984, Pat. No. 4,619,780, which is a division of Ser. No. 574,150, Jan. 26, 1984, Pat. No. 4,521,634, which is a continuation-in-part of Ser. No. 533,915, Sep. 19, 1983, Pat. No. 4,532,364, which is a continuation-in-part of Ser. No. 507,292, Aug. 1, 1983, abandoned.

[51] Int. Cl.[4] .............................................. A24B 3/12

[52] U.S. Cl. ................................................. 131/276
[58] Field of Search ....................................... 131/276

*Primary Examiner*—Vincent Millin
*Attorney, Agent, or Firm*—Arthur L. Liberman

[57] ABSTRACT

Described are the uses of mixtures of hydroxybornyloxybutanes defined according to the generic structure:

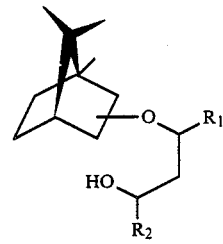

wherein in the mixture in each of the compounds one or $R_1$ or $R_2$ is methyl and the other of $R_1$ or $R_2$ is hydrogen in augmenting or enhancing the aroma or taste of smoking tobacco articles and smoking tobacco compositions.

9 Claims, 6 Drawing Sheets

GLC PROFILE FOR EXAMPLE I.

GLC PROFILE FOR EXAMPLE II.
CRUDE

FIG. 5 NMR SPECTRUM FOR FRACTION 2 OF EXAMPLE II.

USE OF HYDROXYBORNYLOXYBUTANES IN AUGMENTING OR ENHANCING THE AROMA OR TASTE OF SMOKING TOBACCO ARTICLES AND SMOKING TOBACCO COMPOSITIONS

This application is a divisional of U.S. Letters Patent, Ser. No. 837,348 filed on Mar. 7, 1986, now U.S. Pat. No. 4,668,431 issued on May 26, 1987, which, in turn, is a continuation-in-part of application for U.S. Letters Patent, Ser. No. 784,618 filed on Oct. 4, 1985, now U.S. Pat. No. 4,620,041 issued Oct. 28, 1986; which, in turn, is a divisional of application for U.S. Letters Patent, Ser. No. 644,054 filed on Aug. 24, 1984, now U.S. Pat. No. 4,619,780 issued on Oct. 28, 1986; which, in turn, is a divisional of application for U.S. Letters Patent, Ser. No. 574,150 filed on Jan. 26, 1984, now U.S. Pat. No. 4,521,634 issued on June 4, 1985; which, in turn, is a continuation-in-part of application for U.S. Letters Patent, Ser. No. 533,915 filed on Sept. 19, 1983, now U.S. Pat. No. 4,532,364 issued on July 30, 1985; which, in turn, is a continuation-in-part of application for U.S. Letters Patent, Ser. No. 507,292 filed on Aug. 1, 1983, now abandoned.

BACKGROUND OF THE INVENTION

The instant invention provides the mixtures of hydroxybornyloxybutanes defined according to the generic structure:

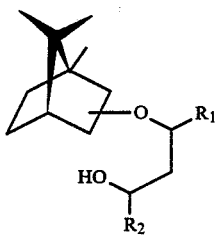

wherein in each of the compounds of the mixture one of $R_1$ or $R_2$ is methyl and the other of $R_1$ or $R_2$ is hydrogen.

Inexpensive woody, cedarwood, incense-like and patchouli-like aromas with incense topnotes are highly desirable in the art of perfumery. Many of the natural materials which provide such fragrances and contribute desired nuances to perfumery compositions as well as perfumed articles including solid or liquid anionic, cationic, nonionic or zwitterionic detergents, perfumed polymers, fabric softener compositions, fabric softener articles, hair preparations, cosmetic powders and the like are high in cost, vary in quality from one batch to another and/or are generally subject to the usual variations of natural products.

U.S. Pat. No. 3,354,225 (Kane) issued on Nov. 21, 1967 (Class 568, Subclass 665) discloses the cedarwood aroma of the compound having the structure:

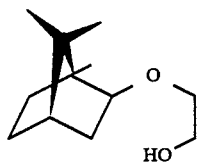

commercially available under the name "Arbinol". The compound having the structure:

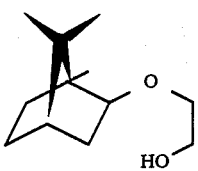

has aroma qualities different in kind and has a substantivity and strength substantially less than the mixture of hydroxybornyloxybutanes of our invention.

BRIEF DESCRIPTIONS OF THE DRAWINGS

FIG. 1 is the GLC profile for the reaction product of Example I of our invention after one hour of reaction, said reaction product containing a mixture of compounds defined according to the generic structure:

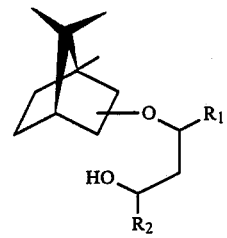

wherein in the mixture in each of the compounds one of $R_1$ or $R_2$ is methyl and the other of $R_1$ or $R_2$ is hydrogen, said mixture including isomers defined according to the structures:

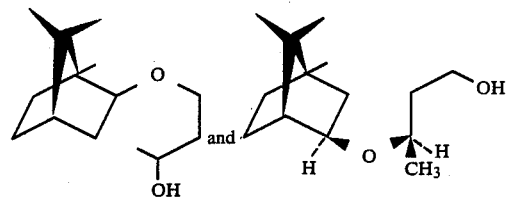

(Conditions: SE-30 column programmed at 160°–220° C. at 8° C. per minute).

FIG. 2 is the GLC profile for the crude reaction product of our invention produced according to Example I defined according to the generic structure:

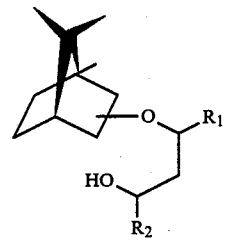

wherein in the mixture in each of the compounds one of $R_1$ or $R_2$ is methyl and the other of $R_1$ or $R_2$ is hydrogen.

FIG. 3 is the GLC profile for bulked distillation fractions 6–16 of the second distillation of the reaction product of our invention containing compounds defined according to the structure:

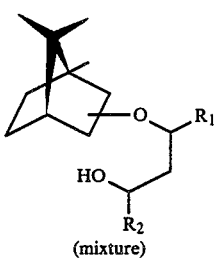

(mixture)

wherein in the mixture in each of the compounds, one of $R_1$ or $R_2$ is methyl and the other of $R_1$ or $R_2$ is hydrogen.

FIG. 4 is the GLC profile for the crude reaction product of Example II containing the mixture of compounds defined according to the structure:

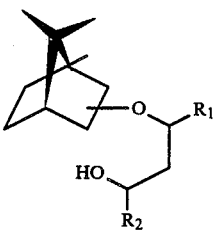

wherein in the mixture one or $R_1$ or $R_2$ is methyl and the other of $R_1$ or $R_2$ is hydrogen.

FIG. 5 is the NMR spectrum for fraction 2 of the distillation product of the reaction product of Example II containing the mixture of compounds defined according to the generic structure:

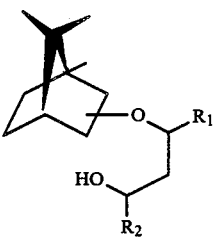

wherein in the mixture in each of the compounds one of $R_1$ or $R_2$ is methyl and the other of $R_1$ or $R_2$ is hydrogen (Conditions: Field strength: 100 MHg; Solvent: $CFCl_3$).

DETAILED DESCRIPTION OF THE DRAWINGS

Figures 6, 7:
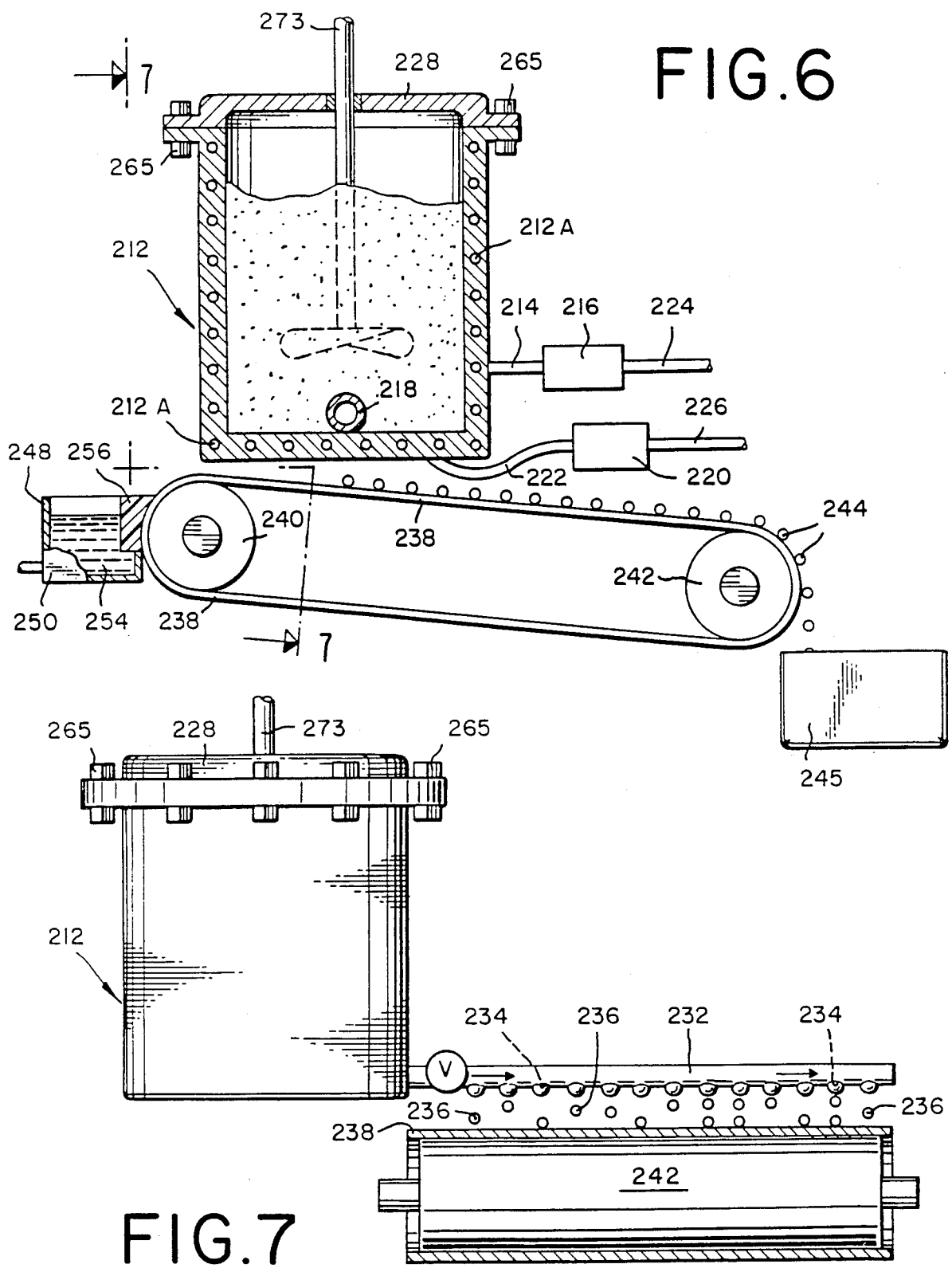
FIG. 6 represents a cut-away side elevation view of apparatus used in forming perfumed polymers which contain embedded therein at least one of the mixtures of hydroxybornyloxybutanes of our invention.
FIG. 7 is a front view of the apparatus of FIG. 6 looking in the direction of the arrows.

Referring to FIGS. 6 and 7, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lowermost portion of the container 212 is maintained at a slightly lower temperature and the material in the container is taken off at such location for delivery through the conduit. Thus, referring to FIGS. 6 and 7, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is a mixture of the hydroxybornyloxybutanes of our invention and other compatible perfumes (if desired) is placed. The container is closed by means of an air-tight lid 228 and clamped to the container by bolts 265. A stirrer 273 traverses the lid or cover 228 in an air-tight manner and is rotatable in a suitable manner. A surrounding cyclinder 212 having heating coils 212A which are supplied with electric current through cables 214 and 222 from rheostats or controls 216 or 220 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 and the control 216 connected thereto through connecting wires 222 and 214 respectively to maintain the lower portion of the container 212 within a temperature range of 220°–270° C.

Thus, the polymer or mixture of polymers added to the container 212 is heated from 10–12 hours, whereafter the perfume composition or perfume material which contains a mixture of the hydroxybornyloxybutanes of our invention is quickly added to the melt. Generally, about 10–45% by weight of the resulting mixture of the perfumery substance containing a mixture of hydroxybornyloxybutanes of our invention is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with a mixture of hydroxybornyloxybutanes of our invention taken alone or taken further together with other perfume substances will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains a mixture of hydroxybornyloxybutanes of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water 254 or some other suitable cooling liquid 254 to insure the rapid cooling of each of the pellets 244. The pellets are then collected from the container 250 and utilized for formation of other functional products, e.g., garbage bags and the like.

THE INVENTION

The present invention provides mixtures of hydroxybornyloxybutanes defined according to the generic structure:

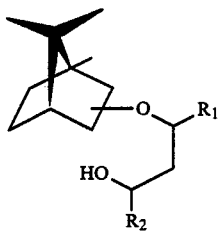

wherein in the mixture, in each of the compounds one of $R_1$ or $R_2$ is methyl and the other of $R_1$ or $R_2$ is hydrogen. Such a mixture of compounds contains a large number of isomers including isomers having the structure:

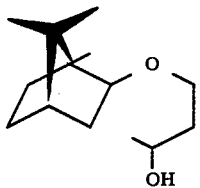

as well optical isomers, for example, those having the structure:

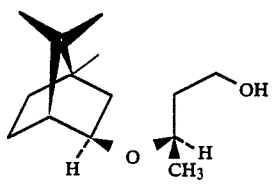

The mixture of hydroxybornyloxybutanes of our invention is Prepared according to a process which comprises reacting camphene having the structure:

with 1,3-dihydroxybutane having the structure:

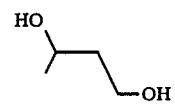

in the presence of an acid catalyst; e.g., a Lewis acid or a Protonic acid catalyst. Thus, the reaction for producing the mixture of hydroxybornyloxybutanes of our invention is shown thusly:

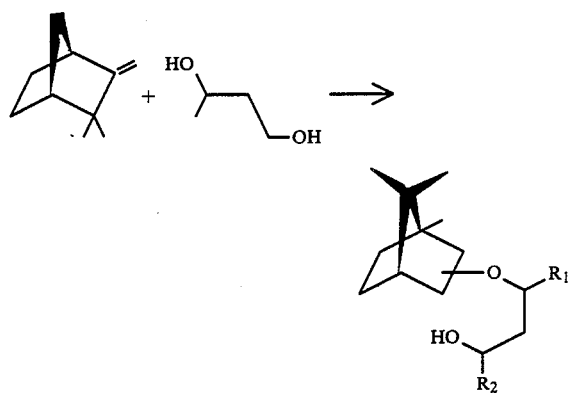

wherein a mixture of compounds is formed and in the mixture in each of the compounds one of $R_1$ or $R_2$ is methyl and the other of $R_1$ or $R_2$ is hydrogen.

The resulting mixture of hydroxybornyloxybutanes of our invention produced according to the process of our invention are capable of augmenting or enhancing the aroma and/or taste of consumable materials including but not limited to foodstuffs, chewing gums, toothpastes, medicinal products, chewing tobaccos, perfumes, perfumed articles, colognes, smoking tobacco and smoking tobacco articles.

Thus, the mixture of hydroxybornyloxybutanes of our invention augment or enhance a cedarwood, incense and patchouli aromas with incense-like topnotes of perfume compositions, colognes and perfumed articles (including but not limited to soaps, anionic, cationic, nonionic or zwitterionic detergents, fabric softener compositions, fabric softener articles, optical brightener compositions, perfumed polymers, hair preparations and the like, thus fulfilling a need in the field of perfumery as well as detergent, cologne, fabric softener and cosmetic manufacture.

In smoking tobacco, smoking tobacco flavoring compositions, substitute smoking tobacco and substitute tobacco flavoring compositions, the mixture of hydroxybornyloxybutanes of our invention produced according to the processes of our invention augment or enhance woody, incense, oriental and patchouli aroma and taste nuances both prior to and on smoking in the mainstream and the side stream.

As stated, supra, the mixture of hydroxybornyloxybutanes of our invention defined according to the generic structure:

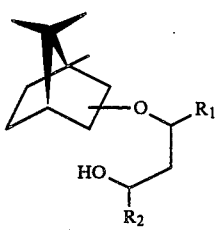

wherein in the mixture one of $R_1$ or $R_2$ is methyl and the other of $R_1$ or $R_2$ is hydrogen may be prepared by reacting camphene having the structure:

with 1,3-dihydroxybutane having the structure:

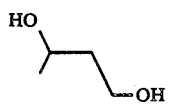

according to the reaction:

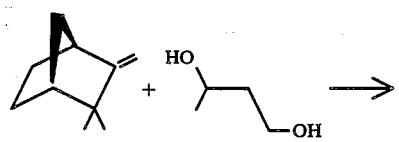

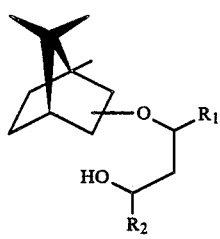

in the presence of a protonic acid catalyst or a Lewis acid catalyst.

Thus, when the reaction takes place in the presence of a catalyst which is a Lewis acid, for example, borontrifluoride etherate, zinc chloride, stannic chloride, diethyl aluminum chloride, ethyl dialuminum chloride or the like, the reaction temperature may range from about 60° C. up to about 100° C. at pressures in the range of from about one atmosphere up to ten atmospheres. Preferably, the reaction when using a Lewis acid takes place at 80° C. at atmospheric pressure and at reflux conditions. The reaction time may vary from about two hours up to about twenty hours depending upon temperature of the reaction. Higher temperatures of reaction give rise to lower times of reaction and lower temperatures of reaction require high times of reaction but a better overall yield of mixture of hydroxybornyloxybutanes of our invention. The mole ratio of 1,3-butanediol having the structure:

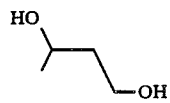

to camphene having the structure:

may vary from about 1:2 up to about 3:1 with a mole ratio of diol:camphene of about 2:1 being preferred. At the end of the reaction the reaction mass is neutralized and the reaction product which is a mixture of hydroxybornyloxybutanes defined according to the generic structure:

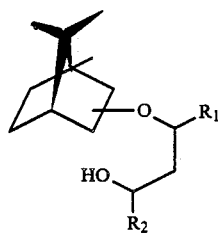

is purified for organoleptic uses as by means of fractional distillation.

When using a protonic acid catalyst, such protonic acids as concentrated sulfuric acid (e.g., 92% aqueous sulfuric acid), concentrated phosphoric acid, paratoluene sulphonic acid and methane sulphonic acid as well as xylene sulphonic acid may be used. When the reaction, to wit:

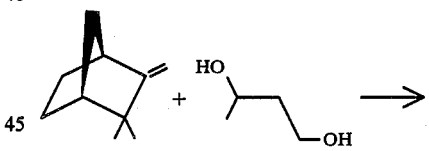

takes place in the presence of a protonic acid, the mole ratio of 1,3-butanediol:camphene may vary from about 3:1 down to about 1:1 with a preferred mole ratio of about 1.5:1 of 1,3-butanediol:camphene. The amount of protonic acid in the reaction mass based on moles camphene reactant may vary from about 0.5% up to about 3% of the camphene reactant with a preferred mole ratio of about 1% of the protonic acid, e.g., concentrated sulfuric acid. The reaction temperature may vary between about 120° C. and about 160° C. with a preferred reaction temperature of from about 135°–150° C. The reaction time may vary from about one hour up to about ten hours. Higher temperatures of reaction give rise to lower times of reaction and lower temperatures of reaction give rise to high times of reaction but a better overall yield. At the end of the reaction the reaction mass is neutralized and the reaction product defined according to the generic structure:

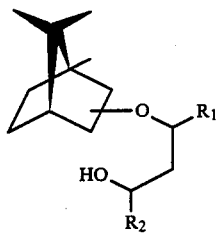

is purified for organoleptic uses by means of fractional distillation.

Furthermore, the mixture of hydroxybornyloxybutanes of our invention are capable of supplying and/or potentiating certain flavor and aroma notes usually lacking in many smoking tobacco flavors and substitute tobacco flavors heretofore provided.

As used herein in regard to smoking tobacco flavors, the terms "alter" and "modify", in their various forms, mean "supplying or imparting flavor character or note to otherwise bland smoking tobacco, smoking tobacco substitutes, or smoking tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of qaulity of aroma or taste) of one or more taste and/or aroma nuances present in the organoleptic impression of smoking tobacco or a smoking tobacco substitute or a smoking tobacco flavor.

Our invention thus provides an organoleptically improved smoking tobacco product and additives therefor, as well as methods of making the same which overcome specific problems heretofore encountered in which specific desired inscence-like, patchouli, spicy and oriental aroma and taste nuances prior to and on smoking in both the main stream and in the side stream are created or enhanced and may be readily controlled and maintained at the desired uniform level regardless of variations in the tobacco components of the blend.

This invention further provides various improved smoking tobacco additives and methods, whereby, various woody, incense-like, oriental and patchouli nuances are imparted (on smoking in the main stream and in the side stream) to smoking tobacco products and may be readily varied and controlled to produce the desired uniformed flavor characteristics, particularly, insofar as "oriental" like tobacco characteristics are concerned.

In carrying out this aspect of our invention, we add to smoking tobacco materials or a suitable substitute therefor (e.g., dried lettuce leaves) an aroma and flavor additive containing as an active ingredient a mixture of hydroxybornyloxybutanes of our invention.

In addition to the mixture of hydroxybornyloxybutanes of our invention other flavoring and aroma additives may be added to the smoking tobacco materials or substitute therefor either separately or in admixture with the mixture of hydroxybornyloxybutanes of our invention as follows:

(i) Synthetic Materials
Beta-ethyl-cinnamaldehyde;
Beta-cyclohomocitral;
Eugenol;
Dipentene;
Beta-Damascenone;
Beta-Damascone;
Maltol;
Ethyl maltol;
Delta-undecalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethylnaphtho[2,1b]furan;
4-Hydroxy hexanoic acid, gamma lactone; and
Polyisoprenoid hydrocarbons defined in Example V of U.S. Pat. No. 3,589,372 issued on June 29, 1971.

(ii) Natural Oils
Celery seed oil;
Coffee extract;
Bergamot oil;
Cocoa extract;
Nutmeg oil; and
Origanum oil.

An aroma and flavoring concentrate containing a mixture of hydroxybornyloxybutanes prepared in accodance with the process of our invention, and, if desired, one or more of the above-identified additional flavoring additives may be added to the smoking tobacco material, to the filter or to the leaf or paper wrapper. The smoking tobacco material may be shredded, cured, cased and blended tobacco material or reconstituted tobacco material or tabacco substitutes (e.g., lettuce leaves) or mixtures thereof.

The proportions of flavoring additives may be varied in accordance with taste but insofar as enhancement or the imparting or natural and/or spicy notes and/or incense notes and/or patchouli notes we have found that satisfactory results are obtained if the proportion by weight of the sum total of one or more of the mixture of hydroxybornyloxybutanes of our invention is between 250 ppm and 1,500 ppm (0.025%–0.15%) of the active ingredients to the smoking tobacco material. We have further found that satisfactory results are obtained if the proportion by weight of the sum total of the mixture of hydroxybornyloxybutanes of our invention is between 2,500 and 15,000 ppm (0.25%–1.50%).

Any convenient method for incorporation of the mixture of hydroxybornyloxybutanes of our invention in the tobacco product may be employed. Thus, the mixture of hydroxybornyloxybutanes of our invention taken alone or along with other flavoring additives may be dissolved in a suitable solvent, such as ethanol, pentane, diether ether and/or other volatile organic solvents and the resulting solution may either be sprayed on the cured, cased and blended tobacco material or the tobacco material may be dipped into such solution. Under certain circumstances, a solution containing a mixture of hydroxybornyloxybutanes of our invention taken alone or taken further together with other flavoring additives set forth above, may be applied by means of a suitable applicator such as a brush or roller on the paper or leaf wrapped for the smoking product, or it may be applied to the filter by either spraying, or dipping, or coating.

Furthermore, it will be apparent that only a portion of the smoking tabacco or substitute therefore need be treated and the thus treated tobacco may be blended with other tobaccos before the ultimate tobacco product is formed. In such cases, the tobacco treated may have a mixture of hydroxybornyloxybutanes of our invention in excess of the amounts or concentrations above-indicated so that when blended with other tabaccos, the final product will have the percentage within the indicated range.

In accordance with one specific example of our invention, an aged, cured and shredded domestic Burley tobacco is sprayed with a 20% ethyl alcohol solution of a mixture of compounds defined according to the generic structure:

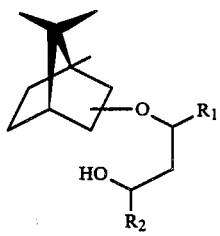

wherein in the mixture in each of the compounds one of $R_1$ or $R_2$ is methyl and the other of $R_1$ or $R_2$ is hydrogen prepared according to Example I, infra in an amount to provide the tobacco composition containing 800 ppm by weight of the above-mentioned mixture of hydroxybornyloxybutanes on a dry basis.

Thereafter, the alcohol is removed by evaporation and the tobacco is manufactured into cigarettes by the usual techniques. The cigarettes, when treated as indicated, have a desired and pleasing aroma prior to smoking which can be described as woody, incense-like, oriental and patchouli-like and on smoking, in the main stream and in the side stream as spicy, oriental-like, turkish tobacco-like, and woody with a slight mouth coating effect.

While our invention is particularly useful in the manufacture of smoking tobacco, such as cigarette tobacco, cigar tobacco and pipe tobacco, other smoking tobacco products formed from sheets tobacco dust or fines may also be used. Likewise, the mixture of hydroxybornyloxybutanes of our invention can be incorporated with materials such as, filter tip materials, seam paste, packaging materials and the like which are used along with tobacco to form a product adapted for smoking. Furthermore, the mixtures of hydroxybornyloxybutanes of our invention can be used to certain tobacco substitutes of natural or synthetic origin (e.g., dried lettuce leaves) and accordingly, the term "tobacco" is used throughout this specification means any composition intended for human consumption by smoking or otherwise whether composed of tobacco plant parts or substitute materials or both.

The following Examples I and II serve to provide processes for preparing the mixtures of hydroxybornyloxybutanes of our invention. The examples following Example II are illustrative of the organoleptic utilities of the mixture of hydroxybornyloxybutanes of our invention.

All parts and percentages given herein are by weight unless otherwise specified.

EXAMPLE I

PREPARATION OF SULFURIC ACID CATALIZED REACTION PRODUCT OF CAMPHENE AND 1,3-DIHYDROXYBUTANE

Reaction:

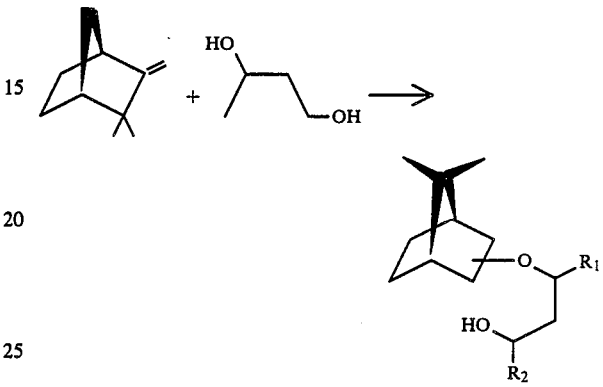

Into a 12 liter distillation flask fitted with stirrer, large condenser, thermometer and dripping funnel, under a nitrogen blanket is placed 2510.0 grams (14.76 moles) of 80% camphene; and 1527.0 grams (16.96 moles) of 1,3-butane diol. With stirring over a period of five minutes, 14.0 grams (0.142 moles of concentrated sulfuric acid (93% sulfuric acid) is added while maintaining the reaction temperature at 45° C.

The reaction mass is then heated to 145° C. with stirring and maintained at a temperature in the range of 137°–145° C. for a period of two hours.

At the end of the two hour reaction period, the reaction mass is cooled to 40° C. and 2 liters of 25% aqueous sodium hydroxide solution is added to the reaction mass. With stirring, the reaction mass is heated to 80° C. and maintained at 80° C. for a period of 15 minutes.

The reaction mass is cooled and separates into two phases; an organic phase and an aqueous phase; the organic phase is distilled on a rushover column yielding the following fractions:

| Fraction No. | Vapor Temp. (°C.) | Liquid Temp. (°C.) | Vacuum mm/Hg. Pressure |
| --- | --- | --- | --- |
| 1 | 80/120 | 100/170 | 4.5/3.0 |
| 2 | 128 | 143 | 3.8 |
| 3 | 130 | 143 | 3.8 |
| 4 | 130 | 150 | 3.8 |
| 5 | 130 | 165 | 3.8 |
| 6 | 145 | 170 | 3.5 |

Fractions 2–5 are bulked and redistilled on a 12" Goodloe column yielding the following fractions:

| Fraction No. | Vapor Temp. (°C.) | Liquid Temp. (°C.) | Vacuum mm/Hg. Pressure |
| --- | --- | --- | --- |
| 1 | 48/60 | 112/120 | 1.2/1.2 |
| 2 | 80 | 121 | 1/2 |
| 3 | 82 | 122 | 1.2 |
| 4 | 82 | 122 | 1.2 |

| Fraction No. | Vapor Temp. (°C.) | Liquid Temp. (°C.) | Vacuum mm/Hg. Pressure |
| --- | --- | --- | --- |
| 5 | 82 | 122 | 1.2 |
| 6 | 82 | 122 | 1.2 |
| 7 | 82 | 122 | 1/2 |
| 8 | 83 | 124 | 1.2 |
| 9 | 84 | 123 | 1.0 |
| 10 | 84 | 123 | 1.0 |
| 11 | 85 | 123 | 1.0 |
| 12 | 85 | 123 | 1.0 |
| 13 | 85 | 123 | 1.0 |
| 14 | 85 | 124 | 1.0 |
| 15 | 85 | 125 | 1.0 |
| 16 | 86 | 127 | 1.0 |
| 17 | 87 | 129 | 1.0 |
| 18 | 89 | 133 | 1.0 |
| 19 | 90 | 145 | 1.0 |
| 20 | 101 | 195 | 1.0 |

Figure 1:
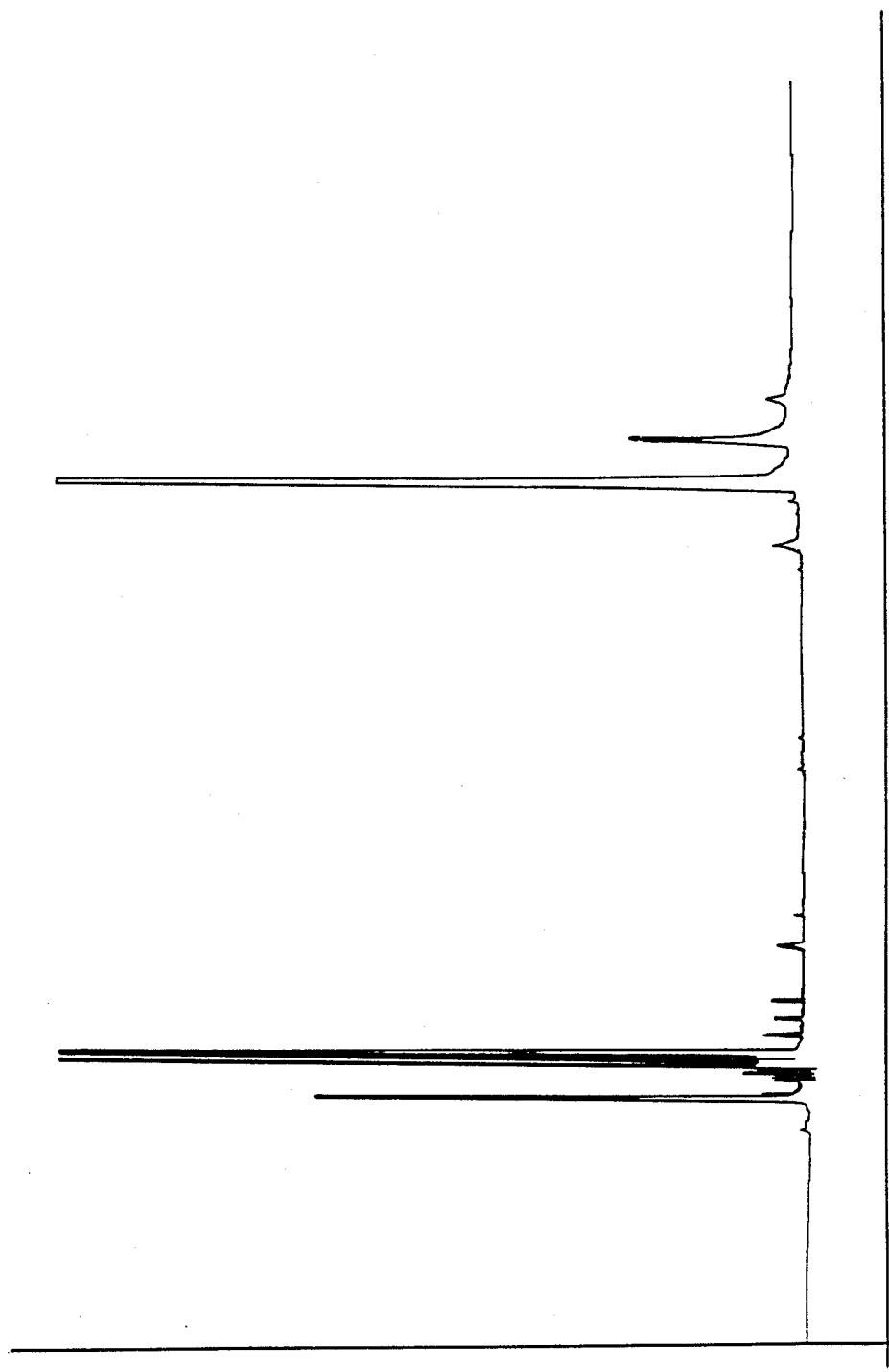

FIG. 1 is the GLC profile from the reaction product after one hour of reaction (Conditions: SE-30 column programmed at 150°-220° C. at 8° C. per minute).

Figure 2:
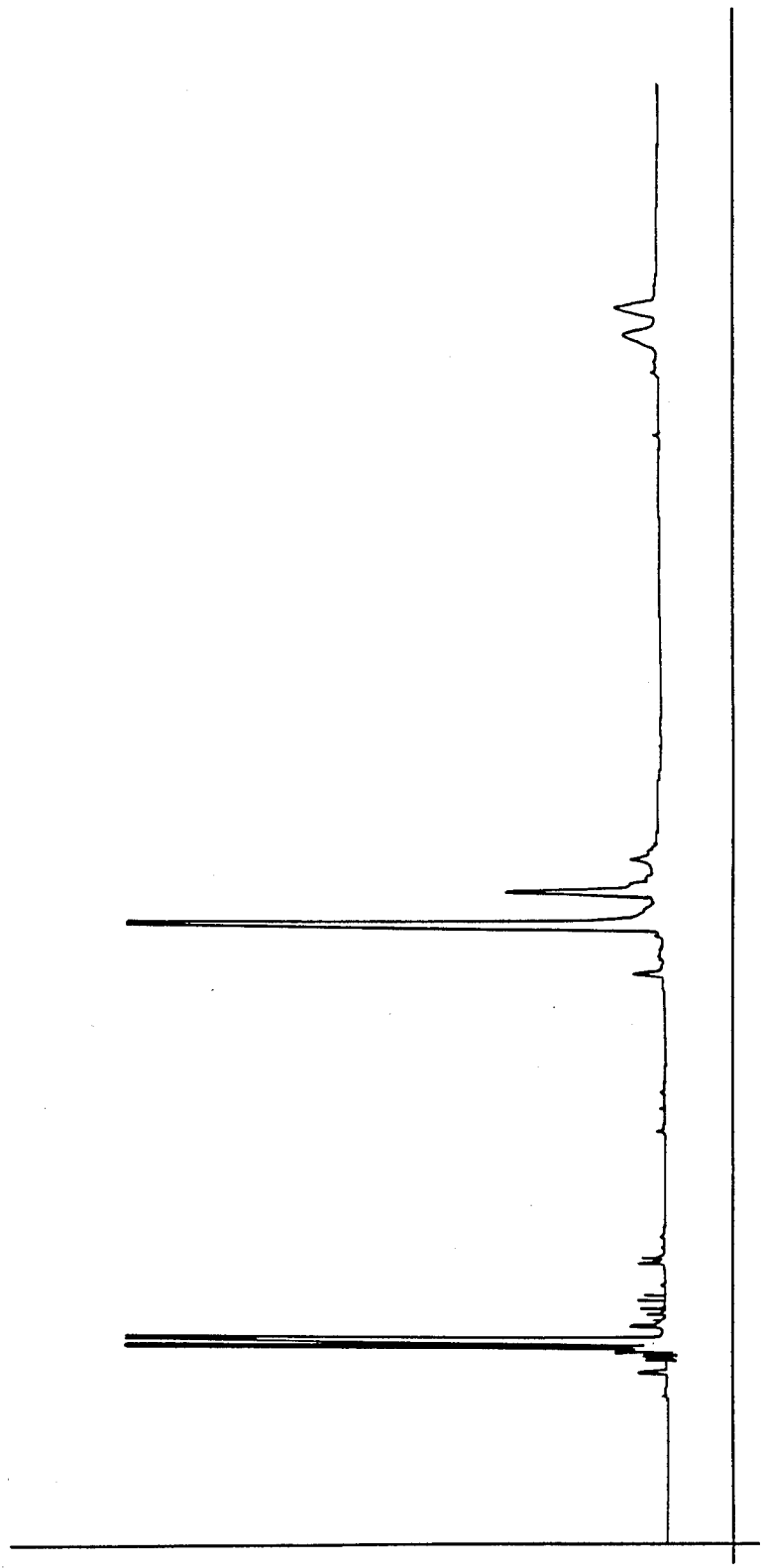

FIG. 2 is the GLC profile for the crude reaction product prior to distillation.

Figure 3:
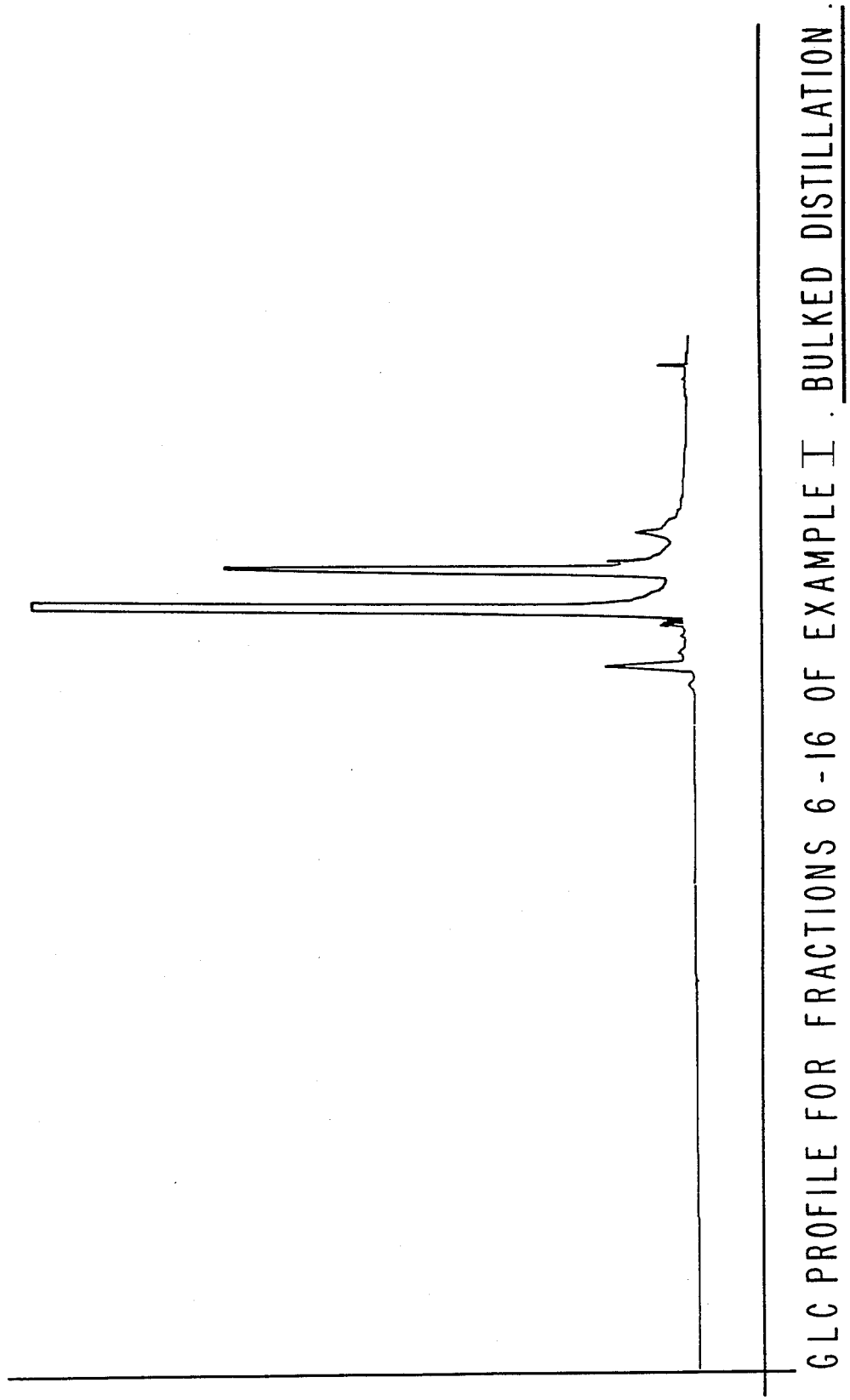

FIG. 3 is the GLC profile for bulked distillation fractions 6–16 of the foregoing second distillation.

EXAMPLE II

PREPARATION OF MIXTURE OF HYDROXYBORNYLOXYBUTANES

Reaction:

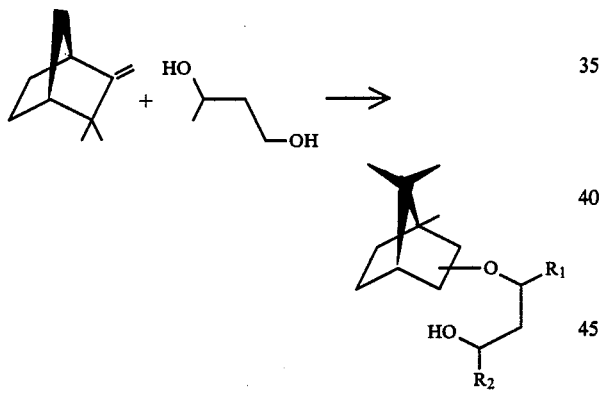

wherein a mixture is formed and in the mixture in each of the compounds one of $R_1$ or $R_2$ is methyl and the other of $R_1$ or $R_2$ is hydrogen.

Into a one liter vessel equipped with a stirrer, thermometer, reflux condenser and having mantle is placed 340 grams of 1,3-butanediol and 10 grams of boron trifluoride. The reaction mass is heated to 80° C. and while maintaining the reaction mass at 80° C., 340 grams of camphene is added over a two hour period. At the end of the camphene feeding period, the reaction mass is stirred at a temperature of 80° C. for a period of 18 hours.

After the 18 hour period, the reaction mass is quenched with water and the reaction mass is washed with saturated sodium carbonate solution until neutral. The aqueous phase is separated from the organic phase. The aqueous phase is extracted with toluene and the toluene extracts are added to the organic phase. The resulting organic material is then charged to an evaporator and the toluene solvent is recovered.

The resulting product is distilled on a column packed with splash saddles yielding the following fractions:

| Fraction No | Vapor Temp. (°C.) | Liquid Temp. (°C.) | Vacuum mm/Hg. Pressure | Weight of Fraction (gms) |
| --- | --- | --- | --- | --- |
| 1 | 93/ | 127/ | 5.0 | 7.0 |
| 2 | 115 | 127 | 5.0 | 15.0 |
| 3 | 123 | 136 | 4.8 | 211.0 |
| 4 | 175 | 220 | 3.8 | 190.0 |

Figure 4:
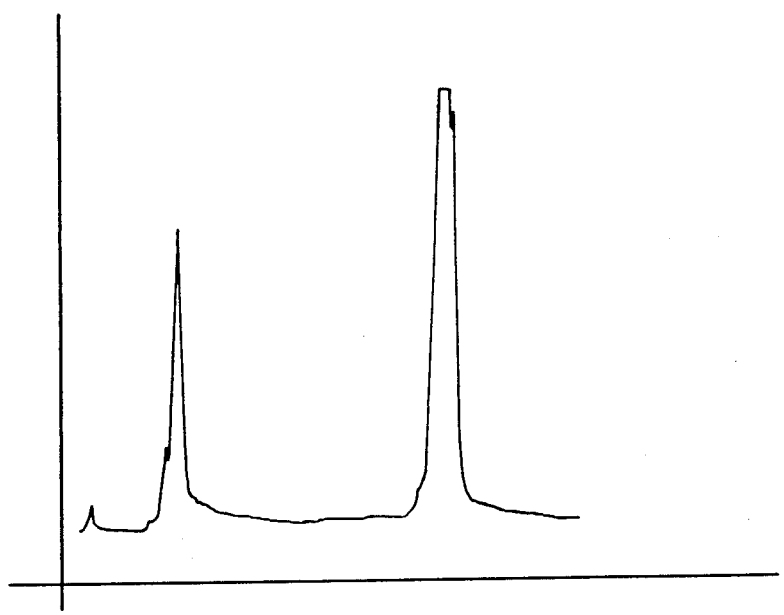

FIG. 4 is the GLC profile for the crude reaction product containing the mixture of compounds defined according to the generic structure:

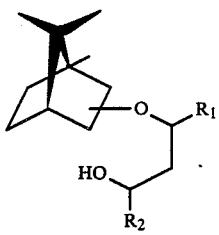

wherein in the mixture in each of the compounds one of $R_1$ or $R_2$ is methyl and the other of $R_1$ or $R_2$ is hydrogen.

Figure 5:
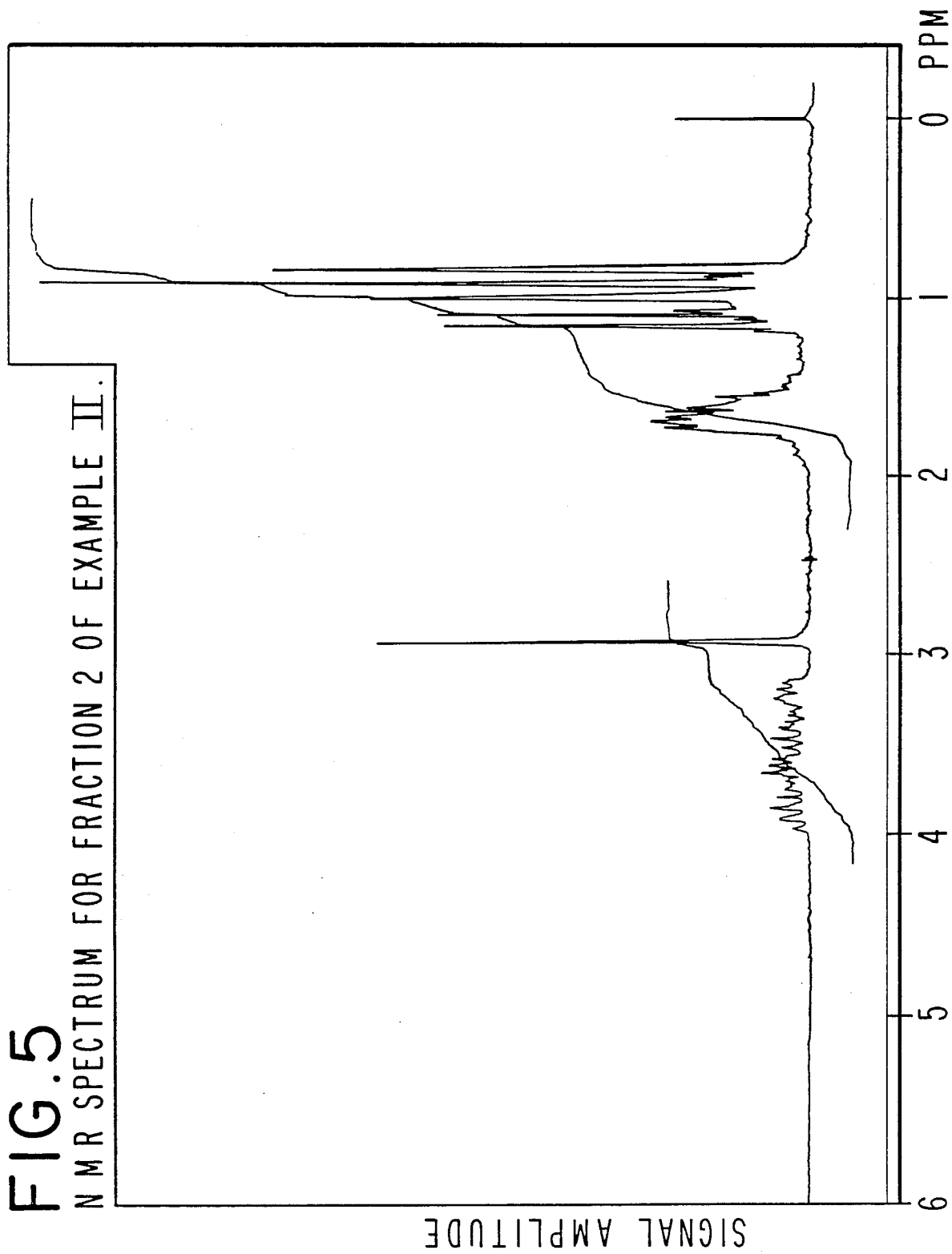

FIG. 5 is the NMR spectrum for fraction 2 of the foregoing distillation product containing the mixture of compounds defined according to the structure:

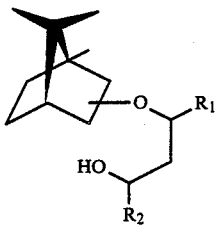

wherein in the mixture in each of the compounds one of $R_1$ or $R_2$ is methyl and the other of $R_1$ or $R_2$ is hydrogen (Conditions: Field strength: 100 MHz; Solvent: $CFCl_3$).

EXAMPLE III

TOBACCO FLAVOR FORMULATION

Cigarettes are produced using the following tobacco formulation:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| $H_2O$ | 5.3 |

At the rate of 0.2%, the following tobacco flavor formulation is applied to all of the cigarettes produced with the above tobacco formulation.

| Ingredients | Parts by Weight |
| --- | --- |
| Ethyl Butyrate | .05 |
| Ethyl Valerate | .05 |
| Maltol | 2.00 |

| Ingredients | Parts by Weight |
| --- | --- |
| Cocoa Extract | 26.00 |
| Coffee Extract | 10.00 |
| Ethyl Alcohol (95%) | 20.00 |
| H₂O | 41.90 |

To 50% of the cigarettes, 50 and 100 ppm of the mixture of compounds defined according to the structure:

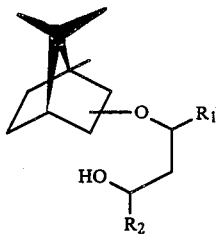

(wherein in the mixture in each of the compounds one of $R_1$ or $R_2$ is methyl and the other of $R_1$ or $R_2$ is hydrogen) produced according to Example I bulked distillation fractions 6–16 are added. These cigarettes are hereinafter called experimental cigarettes and the cigarettes without the mixture of compounds defined according to the structure:

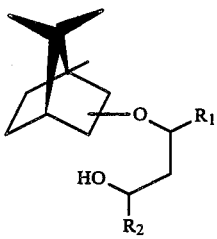

produced according to Example I are hereinafter called "control cigarettes". The control and experimental cigarettes are then evaluated by paired comparison and the results are as follows:

a. In aroma, the experimental cigarettes are found to be more aromatic with a woody, incense, oriental and patchouli aroma and taste.

b. In smoke flavor, the experimental cigarettes are found aromatic, more sweet, more bitter, richer and slightly less harsh in the mouth and more cigarette tobacco-like than the control cigarettes with woody, incense, oriental and patchouli-like aroma and taste nuances.

In summary, the experimental cigarettes containing the mixture of compounds defined according to the generic structure:

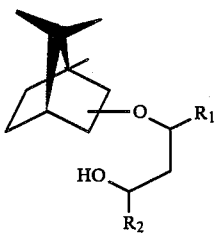

produced according to Example I are found to be woody, incense, oriental and patchouli-like and turkish tobacco-like in the main stream and in the side stream.

All cigarettes both control and experimental are evaluated for smoke flavor with 20 mm cellulose acetate filters.

A similar effect occurs when using the mixture of compounds defined according to the generic structure:

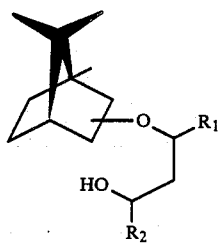

produced according to Example II, bulked fractions 2–4.

What is claimed is:

1. A process for augmenting or enhancing the aroma of a consumable material selected from the group consisting of smoking tobacco articles and smoking tobacco compositions comprising the step of adding to said consumable material, and aroma or taste augmenting or enhancing quantity of a mixture of compounds defined according to the generic structure:

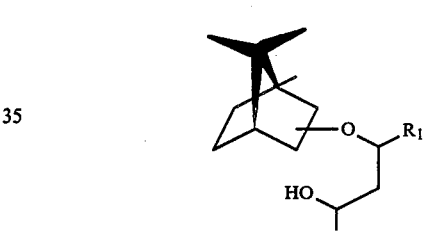

wherein in the mixture in each of the compounds one of $R_1$ or $R_2$ is methyl and the other of $R_1$ and $R_2$ is hydrogen produced according to the process of reacting camphene having the structure:

with 1,3-butanediol having the structure:

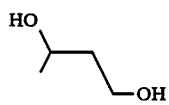

in the presence of an acid catalyst.

2. The process of claim 1 wherein in the process for producing the product, the acid catalyst is a protonic acid.

3. The process of claim 1 wherein in the process for producing the product, the acid catalyst is sulfuric acid.

4. A smoking tobacco composition comprising smoking tobacco and intimately admixed therewith, an aroma or taste augmenting or enhancing quantity of a mixture of compounds defined according to the generic structure:

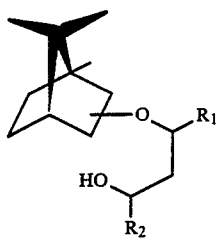

wherein in the mixture in each of the compounds one of $R_1$ or $R_2$ is methyl and the outer of $R_1$ or $R_2$ is hydrogen produced according to the process of reacting camphene having the structure:

with 1,3-butanediol having the structure:

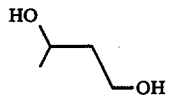

in the presence of an acid catalyst.

5. The composition of claim 4 wherein in the process for producing the product the acid catalyst is a protonic acid.

6. The smoking tobacco composition of claim 4 wherein in the process for producing the product the acid catalyst is sulfuric acid.

7. A smoking tobacco article comprising a shaped cylindrical mass of smoking tobacco; in intimate contact with said smoking tobacco, a wrapper; and in intimate contact with said shaped cylinder at one end thereof; a filter; and in intimate contact with said filter, said wrapper or said smoking tobacco, an aroma or taste augmenting or enhancing quantity of a mixture of compounds defined according to the generic structure:

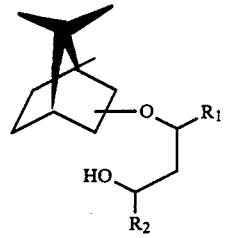

wherein in the mixture in each of the compounds one or $R_1$ or $R_2$ is methyl and the other of $R_1$ or $R_2$ is hydrogen produced according to the process of reacting camphene having the structure:

with 1,3-butanediol having the structure:

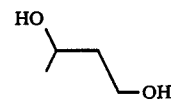

in the presence of an acid catalyst.

8. The smoking tobacco article of claim 7 wherein in the process for producing the product the acid catalyst is a protonic acid.

9. The smoking tobacco article of claim 7 wherein in the process for producing the product the acid catalyst is sulfuric acid.

* * * * *